(12) United States Patent
Xiong et al.

(10) Patent No.: US 9,731,280 B2
(45) Date of Patent: Aug. 15, 2017

(54) FERRITE CATALYST AND PREPARATION METHOD THEREOF

(71) Applicant: Shanghai HuaYi Acrylic Acid Co. Ltd., Shanghai (CN)

(72) Inventors: Desheng Xiong, Shanghai (CN); Tonghao Wu, Shanghai (CN); Ge Luo, Shanghai (CN); Yan Zhuang, Shanghai (CN); Jiangxue Ma, Shanghai (CN); Xiaodong Chu, Shanghai (CN); Jinghua Ji, Shanghai (CN)

(73) Assignee: Shanghai HuaYi Acrylic Acid Co. Ltd., Shanghai (CN)

( * ) Notice: Subject to any disclaimer, the term of this patent is extended or adjusted under 35 U.S.C. 154(b) by 0 days.

(21) Appl. No.: 14/086,313

(22) Filed: Nov. 21, 2013

(65) Prior Publication Data
US 2014/0141965 A1    May 22, 2014

(30) Foreign Application Priority Data

Nov. 21, 2012  (CN) .......................... 2012 1 0475737

(51) Int. Cl.
| | | |
|---|---|---|
| *B01J 23/76* | (2006.01) | |
| *B01J 27/187* | (2006.01) | |
| *B01J 27/185* | (2006.01) | |
| *B01J 23/847* | (2006.01) | |
| *B01J 23/889* | (2006.01) | |
| *B01J 23/00* | (2006.01) | |
| *B01J 23/78* | (2006.01) | |
| *B01J 23/80* | (2006.01) | |
| *B01J 23/881* | (2006.01) | |
| *B01J 23/888* | (2006.01) | |
| *B01J 27/188* | (2006.01) | |
| *B01J 27/198* | (2006.01) | |
| *C07C 5/48* | (2006.01) | |
| *B01J 37/03* | (2006.01) | |
| *B01J 37/08* | (2006.01) | |
| *B01J 37/00* | (2006.01) | |

(52) U.S. Cl.
CPC .......... *B01J 27/187* (2013.01); *B01J 23/005* (2013.01); *B01J 23/007* (2013.01); *B01J 23/78* (2013.01); *B01J 23/80* (2013.01); *B01J 23/8472* (2013.01); *B01J 23/881* (2013.01); *B01J 23/888* (2013.01); *B01J 23/8892* (2013.01); *B01J 27/188* (2013.01); *B01J 27/1853* (2013.01); *B01J 27/198* (2013.01); *C07C 5/48* (2013.01); *B01J 37/0018* (2013.01); *B01J 37/0036* (2013.01); *B01J 37/03* (2013.01); *B01J 37/08* (2013.01); *B01J 2523/00* (2013.01); *C07C 2521/02* (2013.01); *C07C 2523/02* (2013.01); *C07C 2523/22* (2013.01); *C07C 2523/28* (2013.01); *C07C 2523/34* (2013.01); *C07C 2523/745* (2013.01); *C07C 2523/75* (2013.01); *C07C 2523/755* (2013.01); *C07C 2523/78* (2013.01); *C07C 2523/80* (2013.01); *C07C 2527/167* (2013.01); *C07C 2527/236* (2013.01)

(58) Field of Classification Search
CPC ... B01J 23/80; B01J 27/16; B01J 27/18; B01J 27/1853; B01J 23/745; B01J 23/78; B01J 23/8892; C07C 5/48; C07C 5/42
USPC ................ 502/213, 208, 328, 329, 338, 343
See application file for complete search history.

(56) References Cited

U.S. PATENT DOCUMENTS

| | | | | |
|---|---|---|---|---|
| 3,270,080 A | * | 8/1966 | Christmann | ................... 585/622 |
| 3,702,875 A | * | 11/1972 | Manning | ................... B01J 23/74 |
| | | | | 502/304 |
| 3,937,748 A | | 2/1976 | Miklas | |

(Continued)

FOREIGN PATENT DOCUMENTS

| | | |
|---|---|---|
| CN | 1033013 | 5/1989 |
| CN | 1072110 | 5/1993 |
| CN | 1088624 | 8/2002 |
| CN | 101896267 | 11/2010 |

OTHER PUBLICATIONS

Qiu et al., "Effect of added $Sb_2O_4$, $BiPO_4$, or $SnO_2$ on the catalytic properties of $ZnFe_2O_4$ in the oxidative dehydrogenation of butene to butadiene," Applied Catalysis, vol. 51, pp. 235-253, 1989 (abstract only).

Toledo et al., "Oxidative dehydrogenation of 1-butene of Zn—Al ferrites," Journal of Molecular Catalysis A: Chemical, vol. 125, pp. 53-62, 1997.

Office action issued Jun. 3, 2015 in corresponding Chinese patent application and English language translation, 12 pages total.

*Primary Examiner* — Melvin C Mayes
*Assistant Examiner* — James Corno
(74) *Attorney, Agent, or Firm* — Hamre, Schumann, Mueller & Larson, P.C.

(57) ABSTRACT

Disclosed are a ferrite catalyst and preparation methods thereof. The catalyst is provided with a formula below, wherein A is Mg atom, Zn atom or a mixture of both atoms at any ratio; D is one or more atoms selected from the group consisting of Ni, Co, W, Mn, Ca, Mo or V atom; Z is a catalyst carrier, which is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, magnesium carbonate; a=0.01-0.6; b=0-0.30; c is a number balancing each valence; x, y represent the amounts of principal catalyst and carrier Z respectively, wherein the weight ratio y/x=0.5:1-7:1.

$$x(FeA_aD_bO_c)/yZ$$

14 Claims, No Drawings

(56) References Cited

U.S. PATENT DOCUMENTS

| | | | |
|---|---|---|---|
| 3,951,869 A * | 4/1976 | Baker | B01J 23/8892 |
| | | | 502/324 |
| 4,058,577 A | 11/1977 | Baker | |
| 4,083,884 A | 4/1978 | Purdy | |
| 4,150,064 A | 4/1979 | Miklas | |
| 4,332,972 A | 6/1982 | Christmann et al. | |
| 6,028,027 A * | 2/2000 | Baier | B01J 23/78 |
| | | | 502/300 |

* cited by examiner

FERRITE CATALYST AND PREPARATION METHOD THEREOF

TECHNICAL FIELD

The present invention relates to a catalyst for preparing butadiene through oxydehydrogenation of butylene, said catalyst has high conversion of butylene and selectivity to butadiene. The present invention further relates to a method for preparing the catalyst and use of the catalyst in preparation of butadiene through oxydehydrogenation of butylene.

BACKGROUND ART

Butadiene is a monomer with the highest consumption in synthetic rubber industry as well as an important intermediate in producing synthetic resin and organic chemicals, which can be used in preparing butadiene-styrene rubber, butadiene rubber, acrylonitrile-butadiene rubber, chloroprene rubber, ABS resin and the like, and, in a little cases, it may be used in preparing sulfolane, 1,4-butanediol, hexanedinitrile, hexamethylene diamine, butadiene oligomer, the pesticide captan and the like. Butadiene can also be widely used as adhesive, gasoline additive and otherwise. Asia has become the main area in the world in need of butadiene, and the demand for butadiene is in steady increase each year.

The available butadiene in the market is mainly given by extraction of by-products from naphtha cracking. However, with the development in light ethylene raw material and coal-to-olefin technology, there would no longer be great increase in quantity of the naphtha cracking devices, indicating that the yield of butadiene in the future could not meet its increasing demand, resulting in a growing market gap. It is necessary to develop novel processes, which is independent on olefin cracking, for producing butadiene.

Industrialization of the technique of preparing butadiene through oxydehydrogenation of butylene has been realized in 1960s of the 20$^{th}$ century. The catalyst most used in oxydehydrogenation of butylene is ferric spinel catalyst. For instance, Petro-Tex Corp. (U.S.) has disclosed a process for oxydehydrogenation of butylene using ferric spinel catalyst with a conversion of butylene of 78-80% and a selectivity to butadiene of 92-95%. China has developed ferric spinel catalysts including B-02, H-198, W-201 and the like as well in 1980s of the last century, which have been used in industrial production.

Attractive advantages in using ferric spinel catalyst (e.g. ferrite catalyst) are small content of oxygen-containing organic compounds within the by-products generated and simple treatment of wastewater. However, it has also presented some disadvantages, for example, easy happening of complete oxidation and large formation of CO and $CO_2$. Therefore, how to improve the selectivity of the ferrite catalyst is crucial.

A ferrite catalyst is provided with a structure of spinel $AFe_2O_4$ (A represents Zn, Co, Ni, Mg, Cu, etc.), and can be used in oxydehydrogenation reactions through oxidation and reduction of Fe ions and interaction between oxygen ions in crystal and gaseous oxygen. Among the ferrites, zinc ferrite, magnesium ferrite and manganese ferrite are more suitable for oxydehydrogenation of butylene, wherein zinc ferrite shows a higher selectivity to butadiene than that of other ferrites (E-Y. Qiu, L.-T. Weng, E. Sham, P. Ruiz, B. Delmon, appl. Catal., Vol. 51, Page 235, 1989).

It is known that the activity of a catalyst can be influenced by its preparation process and elementary composition, and the catalytic activity in oxydehydrogenation and the selectivity to butadiene of the catalyst can be enhanced by improving the preparation process, adding helpful metal elements or applying pro- or post-treatment on the catalyst.

For example, it has been reported in U.S. Pat. No. 3,937,748 by Petro-Tex Chemical Corp. that a ferrite catalyst prepared through co-precipitation with ammonia as a precipitant has higher catalytic activity and longer operation life as compared with those of ferrite catalysts prepared by high-temperature solid-state reaction. It has also been reported in Chinese patent applications CN1033013, CN1072110 and CN1088624 by Lanzhou Institute of Chemical Physics (Chinese Academy of Sciences) that ammonia can be used as a precipitant in preparing ferrite catalyst through co-precipitation, and all of these patent applications have discussed in detail of the effects of formulation, preparing process, and process parameters and the like of the ferrite catalyst on the performance of the catalyst.

Additionally, the performance of the ferrite catalyst can further be improved by adding other active components, for example, Ni, Co, Ba, Sr, K, Mo, Bi and so forth into the catalyst. Some metals can enter the framework of the spinel and replace Fe or Zn within the ferrite catalyst, and the presence of which changes the activity and selectivity of the catalyst, especially when Fe is substituted with Al or Cr, resulting in an evident enhance in catalyst activity (J. Mol. Catal. A, Vol. 125, Page 53, 1997).

In U.S. Pat. No. 4,058,577 it is described that when a zinc ferrite catalyst is added with a proper amount of manganese carbonate component, the stability, activity and selectivity of the catalyst can be greatly improved.

In U.S. Pat. No. 4,083,884 it is reported that by-products of acetaldehyde, furan, and acraldehyde etc. from the reaction can be reduced by adding 1-3% (by weight) of calcium oxide into the ferrite catalyst.

In U.S. Pat. No. 4,332,972 it is reported that after adding 1.5 wt % of zinc carbonate into the zinc ferrite catalyst, both the conversion and selectivity of the catalyst are greatly improved with a conversion of butylene of 71.9% and selectivity to butadiene of 93.6% after reacting for 572 hours.

Proper activating treatment on the catalyst can also improve the performance of the catalyst. For example, it has been reported in U.S. Pat. No. 4,150,064 that activating a ferrite catalyst with vapor at about 450° C. can improve the conversion and selectivity of the catalyst.

Attractive advantages of the ferrite catalyst are small content of oxygen-containing organic compounds within the by-products generated and simple treatment of wastewater. However, for the available ferrite catalysts, there is still room for improvement in both selectivity to butadiene and conversion of reaction. Furthermore, it is found that both the raw material butylene and the product butadiene are easy to be deep oxidized under the reaction temperature to generate $CO_2$ and CO when available ferrite catalysts are used.

Therefore, there is still need in the art to develop a ferrite catalyst for preparing butadiene through oxydehydrogenation of butylene, wherein the catalyst not only presents high conversion of butylene and selectivity to butadiene, but also improves the situation of deep oxidation both in the raw material butylene and the product butadiene under the temperature for oxydehydrogenation with this ferrite catalyst.

SUMMARY

One object of the invention is to provide a catalyst for preparing butadiene through oxydehydrogenation of butylene, wherein the catalyst presents high conversion of butylene and selectivity to butadiene, and improves the situation of deep oxidation both in the raw material butylene and the product butadiene under the temperature for oxydehydrogenation with the ferrite catalyst.

Another object of the invention is to provide a method for preparing the catalyst, which produces catalyst with higher conversion of butylene and selectivity to butadiene as compared with the conventional preparation methods.

Another object of the invention is to provide use of the ferrite catalyst in preparing butadiene through oxydehydrogenation of butylene.

Therefore, one aspect of the invention is to provide a ferrite catalyst having the following general formula:

$$x(FeA_aD_bO_c)/yZ$$

wherein,

A is Mg atom, Zn atom or a mixture of both atoms at any ratio;

D is one or more atoms selected from the group consisting of Ni, Co, W, Mn, Ca, Mo or V atom;

Z is a catalyst carrier, which can be one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, magnesium carbonate;

a=0.01-0.6;

b=0-0.30;

c is a number balancing each valence;

x, y represent the amounts of principal catalyst and carrier Z respectively, wherein y/x=0.5:1-7:1 (by weight).

Another aspect of the invention relates to a method for preparing the catalyst of the invention described above, which comprises the following steps:

(1) dissolving the chemical precursors of the desired components into a solution to obtain a mixed slurry;

(2) adding to the mixed slurry a precipitant to adjust the pH thereof to 7.0-9.0, to obtain a precipitated slurry;

(3) mixing the precipitated slurry with the carrier powder and calcining under a temperature of 500-600° C. to obtain the catalyst.

Another aspect of the invention relates to a method for preparing the catalyst of the invention described above, which comprises the following steps:

(1) dissolving the chemical precursors of the desired components and a carrier into a solution to obtain a mixed slurry;

(2) adding to the mixed slurry a precipitant to adjust the pH thereof to 7.0-9.0, to obtain a precipitated slurry;

(3) calcining the precipitated slurry under a temperature of 500-600° C. to obtain the catalyst.

Another aspect of the invention relates to use of the catalyst prepared by the method of the invention in preparing butadiene through gas-phase oxydehydrogenation of butylene.

DETAILED DESCRIPTION

1. Ferrite Catalyst

The present invention relates to a ferrite catalyst, which can provide the reaction of gas-phase oxydehydrogenation of butylene in preparing butadiene with improved conversion of butylene and selectivity to butadiene.

The ferrite catalyst of the invention has the following general formula:

$$x(FeA_aD_bO_c)/yZ$$

wherein,

A is Mg atom, Zn atom or a mixture of both atoms at any ratio;

a=0.01-0.6, preferably a=0.1-0.5, more preferably 0.2-0.4. In an embodiment of the invention, a is within a range defined by any two selected from 0.01, 0.6, 0.1, 0.5, 0.2 and 0.4 as end points.

D is one or more atoms selected from the group consisting of Ni, Co, W, Mn, Ca, Mo or V atom; preferably one or more selected from the group consisting of Ni, Co, Mn or V atom.

In a preferred embodiment of the invention, D represents mixed-atom of Mn atom and Ni and/or Co atom, wherein the molar mixing ratio of Mn atom to Ni and/or Co atom is 10:1-1:10, preferably 5:1-1:5, more preferably 2:1-1:2, most preferably 1.5:1-1:1.5.

b=0-0.30, preferably b=0.01-0.20, more preferably 0.05-0.15, most preferably 0.08-0.10. In a preferred embodiment of the invention, b is within a range defined by any two selected from 0.01, 0.20, 0.05, 0.15, 0.08 and 0.10 as end points.

Z is a catalyst carrier, which can be one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, magnesium carbonate; preferably one or more selected from the group consisting of calcium phosphate, aluminum dihydrogen phosphate, ferric phosphate, magnesium phosphate, zinc phosphate, Mg—Al hydrotalcite.

c is a number balancing each valence;

x, y represent the amounts of the principal catalyst and carrier Z respectively, wherein y/x=0.5:1-7:1 (by weight), preferably 0.8:1-6:1 (by weight), more preferably y/x=1:1-5:1 (by weight), most preferably 1.2:1-4:1, optimally 1.5:1-3:1. In a preferred embodiment of the invention, based on 100 parts by weight of the ferrite precursor powder, the amount of the carrier powder is within a range defined by any two selected from 50, 700, 80, 600, 100, 500, 120, 400, 150 and 300 parts by weight as end points.

For the catalyst of the invention, one key point in improving the conversion of butylene and selectivity to butadiene is adopting a specific combination of the catalyst and the catalyst carrier. As is demonstrated in the following working examples and comparison examples, when the weight ratio between the catalyst and the carrier falls out of the range defined by the invention, the conversion of butylene and/or selectivity to butadiene would be decreased.

2. Preparation of the Ferrite Catalyst

A. The Ferrite Catalyst of the Invention can be Prepared by the Following Procedures:

(1) Dissolving the Chemical Precursors of the Desired Components into a Solution to Obtain a Mixed Slurry;

The chemical precursors can be water-soluble, lipid-soluble or insoluble depending on the producing process. In an embodiment of the invention, water as a reaction medium is used, and thereby the chemical precursors should be water-soluble. Non-restrictive examples of proper water-soluble chemical precursors are, for example, water-soluble nitrates, chlorides, sulfates of metal elements and the like, preferably nitrates.

In a preferred embodiment of the invention, ferric nitrate (e.g. ferric nitrate nonahydrate), zinc nitrate (e.g. zinc nitrate hexahydrate), manganese nitrate, magnesium nitrate (e.g. magnesium nitrate hexahydrate) and/or nickel nitrate (e.g. nickel nitrate hexahydrate) are used as the chemical precursors.

In a preferred embodiment of the invention, metal nitrates are used as the chemical precursors, which can be dissolved in water to form an aqueous solution, facilitating the subsequent alkalization and precipitation steps. There is no specific limitation on the concentration of the aqueous solution formed, provided that the amounts of metal elements can satisfy the proportion requirement of the final ferrite catalyst.

In another preferred embodiment of the invention, the steps for forming the mixed slurry include to weight the ferric nitrate, zinc nitrate, and manganese nitrate and dissolve same in water with a molar ratio of Fe:Zn:Mn=1:0.2-0.5:0.010-0.020.

In another preferred embodiment of the invention, the steps for forming the mixed slurry include to weight the ferric nitrate, zinc nitrate, magnese nitrate, and nickel nitrate and dissolve same in water with a molar ratio of Fe:Zn:Mg; Ni=1:0.3-0.4; 0.035-0.055:0.010-0.020.

(2) To the Mixed Slurry is Added a Precipitant to Adjust the pH Thereof to 7.0-9.0, to Obtain a Precipitated Slurry The method of the invention includes a step of adding a precipitant into the mixed slurry obtained in the step described above. There is no specific limitation on the precipitant, and any precipitant known in the art can be used. In a preferred embodiment of the invention, the precipitant is selected from the group consisting of ammonia, pyridine, trimethylamine, ammonium bicarbonate, ammonium carbonate or a mixture of two or more of them at any ratio. In an embodiment of the invention, the precipitant can be used in the form of aqueous solution.

During the precipitant is added, the pH of the mixed slurry is controlled to be 7.0-9.0, preferably 72-8.8, most preferably 7.5-8.5, most preferably 7.8-8.2.

In an embodiment of the invention, the pH is within a range defined by any two selected from 7.0, 9.0, 7.2, 8.8, 7.5, 8.5, 7.8, 8.2 as end points.

The precipitation step of the invention itself is convention. Those ordinary skilled in the art can perform a proper precipitation procedure easily according to their expertise. For example, agitation can be carried out simultaneously with the addition of the precipitant to ensure a sufficient mixing of the precipitant and the metal nitrates to obtain a mixture of precipitated slurry and the like.

After the precipitated mixed slurry is obtained, the method of the invention can further includes steps of filtering, washing, drying, heat treatment and grinding, to give a solid powder (hereinafter referred to as "ferrite precursor" powder).

In the method of the invention, the particular methods of filtering, washing, drying, heat treatment and grinding are known in the art. Those ordinary skilled in the art can determine the particular procedure easily after reading the disclosure of the invention.

In a preferred embodiment of the invention, after the addition of the precipitant, the mixture is filtered, and washed to neutral with water. The obtained filter cake is dried and heat treated by heating to 450-700° C. for 2-24 hours. The remained solid material is then subjected to grind and sieve to obtain a ferrite precursor powder with a particle size smaller than 60 meshes.

In another preferred embodiment of the invention, after the addition of the precipitant, the slurry is aged under room temperature for 0.5-4 hours, preferably 1-2 hours, and then filtered, and washed to neutral with water. The obtained filter cake is placed in an oven under a temperature of 80-150° C. for drying. The dried solid is heat treated by heating to 450-700° C., preferably to 500-650° C., more preferably to 520-620° C. under atmosphere for 2-24 hours, more preferably 3-22 hours, more preferably 5-18 hours. The remained solid material is then subjected to grind and sieve to obtain a powder with a particle size smaller than 60 meshes, more preferably smaller than 80 meshes, most preferably smaller than 100 meshes, to obtain the ferrite precursor powder. If the particle size is too large, it would disadvantageously affect the performance of the catalyst finally prepared.

(3) The Obtained Ferrite Precursor Powder is Mixed with a Carrier, Molded, Heat Treated Again to Give the Catalyst The catalyst carrier suitable for the method of the invention is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, and magnesium carbonate; preferably one or more selected from the group consisting of calcium phosphate, aluminum dihydrogen phosphate, ferric phosphate, magnesium phosphate, zinc phosphate, and Mg—Al hydrotalcite.

Similarly, before being mixed with the ferrite precursor, the carrier also needs to be grinded and sieved, to obtain a powder with a particle size smaller than 60 meshes, preferably smaller than 80 meshes, most preferably smaller than 100 meshes. If the particle size is too large, it would also disadvantageously affect the performance of the catalyst finally prepared.

Then, the grinded ferrite precursor powder and carrier powder are mixed. There is no specific limitation on suitable method of mixing, and the mixture above can be mixed with any method known in the art. For example, the mixture can be mixed homogeneously through regular mechanical agitation. The relative weight of the carrier powder and the ferrite precursor powder is controlled to be a weight ratio of 0.5:1-7:1, preferably 0.8:1-6:1, more preferably y/x=1:1-5:1, most preferably 1.2:1-4:1, optimally 1.5:1-3:1.

In a preferred embodiment of the invention, based on 100 parts by weight of the ferrite precursor powder, the amount of the carrier powder is within a range defined by any two selected from 50, 700, 80, 600, 100, 500, 120, 400, 150 and 300 parts by weight as end points.

Next, 1-5 wt %, preferably 2-4 wt %, more preferably 2.5-3.5 wt % of graphite powder, based on the total mass, is mixed into the mixture powder, and then molding.

There is no specific limitation on the shape of the catalyst, and it can be in any shape known in the art, for example, cuboid, cube, cylinder, sphere, trefoil and the like.

The molded solid is then calcined in oxygen-containing atmosphere under a temperature of 500-600° C. for 0.5-24 hours.

There is no specific limitation on proper oxygen-containing atmosphere, provided that the oxygen content therein is higher than 5 volume %, preferably higher than 8 volume %, with inert gases for balance. For cost consideration, the calcination is preferably carried out in air.

The temperature for the calcination is preferably 520-580° C., more preferably 540-560° C. In a preferred embodiment of the invention, the calcination is carried out under a temperature within a range defined by any two selected from 500° C., 600° C., 520° C., 580° C., 540° C. and 560° C. as end points.

The calcination duration is preferably for 1-20 hours, preferably 2-10 hours, more preferably 3-8 hours, most preferably 4-6 hours. In an embodiment of the invention, the calcination duration is within one defined by any two selected from 0.5, 24, 1, 20, 2, 10, 3, 8, 4 and 6 hours as end points.

B. The Catalyst of the Invention Can Also be Prepared by the Following Procedures (1) Mixing the Solution of the Chemical Precursors of the Desired Components and the Carrier, to Obtain a Mixed Slurry Depending on the process, the chemical precursors can be water-soluble, lipid-soluble or insoluble. In an embodiment of the invention, water as a reaction medium is used, and thereby the chemical precursors should be water-soluble. Non-restrictive examples of suitable water-soluble chemical precursors are, for example, water-soluble nitrates, chlorides, sulfates of metal elements and the like, preferably nitrates.

In a preferred embodiment of the invention, ferric nitrate (e.g. ferric nitrate nonahydrate), zinc nitrate (e.g. zinc nitrate hexahydrate), manganese nitrate, magnesium nitrate (e.g. magnesium nitrate hexahydrate) and/or nickel nitrate (e.g. nickel nitrate hexahydrate) are used as the chemical precursors.

In a preferred embodiment of the invention, metal nitrates are used as the chemical precursors, which can be dissolved in water to form an aqueous solution, facilitating the subsequent step of alkalization and precipitation. There is no specific limitation on the concentration of the aqueous solution formed, provided that the amounts of metal elements satisfy the proportion requirement of the final ferrite catalyst.

In another preferred embodiment of the invention, the steps for forming the mixed slurry include to weight the ferric nitrate, zinc nitrate, and manganese nitrate and dissolve same in water with a molar ratio of Fe:Zn:Mn=1:0.2-0.5:0.010-0.020.

In another preferred embodiment of the invention, the steps for forming the mixed slurry include to weight the ferric nitrate, zinc nitrate, magnesium nitrate, and nickel nitrate and dissolve same in water with a molar ratio of Fe:Zn:Mg:Ni=1:0.3-0.4:0.035-0.055:0.010-0.020.

The catalyst carrier suitable for the method of the invention is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, and magnesium carbonate; preferably one or more selected from the group consisting of calcium phosphate, aluminum dihydrogen phosphate, ferric phosphate, magnesium phosphate, zinc phosphate, and Mg—Al hydrotalcite.

Similarly, before being mixed with the solution of the ferrite precursor, the carrier also needs to be grinded and sieved, to obtain a powder with a particle size smaller than 60 meshes, preferably smaller than 80 meshes, most preferably smaller than 100 meshes. If the particle size is too large would, it will also disadvantageously affect the performance of the catalyst finally prepared.

There is no specific limitation on suitable method for mixing, and it can be any mixing method known in the art. In an embodiment of the invention, vigorous stirring is used in mixing the materials into a suspension.

The relative weight of the carrier powder and the ferrite precursor powder is controlled to a weight ratio of 0.5:1-7:1, more preferably 0.8:1-6:1, even more preferably y/x=1:1-5:1, most preferably 1.2:1-4:1, and even most preferably 1.5:1-3:1.

In a preferred embodiment of the invention, based on 100 parts by weight of the ferrite catalyst, the amount of the carrier powder used is within a range defined by any two selected from 50, 700, 80, 600, 100, 500, 120, 400, 150 and 300 parts by weight as end points.

(2) To the Mixed Slurry is Added a Precipitant, Adjusting the pH Thereof to be 7.0-9.0 to Obtain a Precipitated Slurry The method of the invention includes a step of adding a precipitant into the mixed slurry obtained in the step described above. There is no specific limitation on the precipitant, and any precipitant known in the art can be used. In a preferred embodiment of the invention, the precipitant is selected from the group consisting of ammonia, pyridine, trimethylamine, ammonium bicarbonate, ammonium carbonate or a mixture thereof at any ratio. In an embodiment of the invention, the precipitant can be used in the form of aqueous solution.

After the precipitant is added, the pH of the mixed slurry of the invention is controlled at 7.0-9.0, preferably 7.2-8.8, more preferably 7.5-8.5, most preferably 7.8-8.2.

In an embodiment of the invention, the pH is within a range defined by any two selected from 7.0, 9.0, 7.2, 8.8, 7.5, 8.5, 7.8, 8.2 as end points.

The precipitation step of the invention itself is conventional. Those ordinary skilled in the art can perform proper precipitation procedure easily according to their expertise. However, in order to achieve a uniform mixing, the stirring is required to be carried out simultaneously with the addition of the precipitant to ensure a sufficient mixing of the precipitant and the metal nitrates as well as the formed metal catalyst and the catalyst carrier to give a mixture of the precipitated slurry and the like.

After the precipitated mixed slurry is obtained, the method of the invention further includes steps of filtering, washing, drying, heat treatment and grinding, to give a solid powder (hereinafter referred to as "ferrite precursor" powder).

In the method of the invention, the methods of filtering, washing, drying, heat treatment and grinding themselves are known in the art. Those ordinary skilled in the art can determine the particular procedure easily after reading the disclosure of the invention.

In a preferred embodiment of the invention, after the addition of the precipitant, the mixture is filtered, and washed to neutral with water. The obtained filter cake is dried and heat treated by heating to 200-350° C. for 2-24 hours. The remained solid material is then subjected to grind and sieve, to obtain a ferrite precursor powder with a particle size smaller than 60 meshes.

In another preferred embodiment of the invention, after the addition of the precipitant, the slurry is aged at room temperature for 0.5-4 hours, preferably 1-2 hours, and then filtered and washed to neutral with water. The obtained filter cake is dried in an oven at a temperature of 80-150° C. The dried solid is heat treated by heating to 200-350° C., preferably to 220-330° C., more preferably to 250-300° C. at atmosphere for 2-24 hours, more preferably 3-22 hours, most preferably 5-18 hours. The remained solid material is then subjected to grind and sieve to obtain a powder with a particle size smaller than 60 meshes, more preferably smaller than 80 meshes, most preferably smaller than 100 meshes, obtaining the catalyst precursor powder. If the particle size is too large, it would disadvantageously affect the performance of the catalyst finally prepared.

(3) The Obtained Catalyst Precursor Powder is Molded, and Heat Treated Again to Give the Catalyst Next, 1-5 wt %, preferably 2-4 wt %, more preferably 2.5-3.5 wt % of graphite powder, based on the total mass, is mixed into the catalyst precursor powder, and then molding.

There is no specific limitation on the shape of the catalyst, and it can be any shape known in the art, for example, cuboid, cube, cylinder, sphere, trefoil and the like.

The molded solid is then calcined in oxygen-containing atmosphere under a temperature of 500-600° C. for 0.5-24 hours.

There is no specific limitation on proper oxygen-containing atmosphere, provided that the oxygen content therein is higher than 5 volume %, preferably higher than 8 volume %, with inert gases for balance. For cost consideration, the calcination is more preferred to be carried out in air.

The temperature for the calcination is preferably 520-580° C., more preferably 540-560° C. In a preferred embodiment of the invention, the calcination is carried out under a temperature within a range defined by any two selected from 500° C., 600° C., 520° C., 580° C., 540° C. and 560° C. as end points.

The calcination duration is preferably for 1-20 hours, more preferably 2-10 hours, most preferably 3-8 hours, optimally 4-6 hours. In an embodiment of the invention, the calcination duration is within a range defined by any two selected from 0.5, 24, 1, 20, 2, 10, 3, 8, 4 and 6 hours as end points.

3. Use of the Ferrite Catalyst of the Invention

The ferrite catalyst of the present application is suitable for preparing butadiene through gas-phase oxydehydrogenation of butylene. A suitable reaction includes the following steps: preheating a mixture of the raw material butylene, vapor, air and a dilute gas and passing same through the catalyst bed for oxydehydrogenation under the following conditions: temperature, 250-550° C.; reaction space velocity (for the raw material butylene), 100-1000 h$^{-1}$; the molar concentration of butylene within the reaction gas, 1-20%; and the molar ratio of butylene:oxygen:vapor:dilute gas is 1:0.2-2:1-20:0-20; the dilute gas is one selected from the group consisting of nitrogen, argon or helium gas.

In one embodiment of the invention, the gas-phase oxydehydrogenation of butylene for preparing butadiene includes the following steps: preheating a mixture of the raw material butylene, vapor, air and dilute gas, and passing same through the catalyst bed for oxydehydrogenation under the following conditions: temperature, 300-450° C.; reaction space velocity (for the raw material butylene), 300-600 h$^{-1}$; the molar concentration of butylene, 4-12%; and the molar ratio of butylene:oxygen:vapor:dilute gas: 1:0.5-1.0:3-16:0-10; the dilute gas is nitrogen.

In the reaction of gas-phase oxydehydrogenation of butylene in the invention for preparing butadiene, a mixed catalyst of phosphates and ferrites prepared by the method of the invention is used in the catalyst bed.

The raw material butylene can be 1-butylene, trans-butylene-2, cis-butylene-2, a mixture of two or more thereof.

Next, the invention is further described by way of the Examples. In the following Examples, the "conversion of butylene" and "selectivity to butadiene" can be calculated by the formulas:

Conversion of butylene (%)=[(butylene amount before reaction−butylene amount after reaction)/butylene amount before reaction]×100%

Selectivity to butadiene (%)=(butadiene amount generated in reaction/butylene amount reacted)×100%

EXAMPLE 1

1. Preparation of Catalyst 404 g of ferric nitrate nonahydrate, 119 g of zinc nitrate hexahydrate, 5.37 g of manganese nitrate solution with a concentration of 50% (by weight) were weighted and dissolved in 1000 ml of distilled water (25° C.), wherein the molar ratio of Fe, Zn and Mn was 1:0.4:0.015; to the solution was added ammonia with a concentration of 20 mol/l dropwise until the pH of the solution reached 7.5. After the addition, the slurry was heated up to 70° C. and stirred for 1 hour before cooling to 25° C., and then filtered, washed to neutral with distilled water.

The obtained filter cake was placed in an oven at 110° C. for drying for 24 hours. The dried solid was subjected to grind, and sieve to give a powder smaller than 80 meshes and then heated up to 650° C. for heat treatment under air atmosphere for 6 hours to give a ferrite precursor powder.

The obtained ferrite precursor powder was homogeneously mixed with calcium phosphate powder and graphite by a mechanical agitator, wherein the weight ratio between calcium phosphate powder and ferrite precursor powder was 2:1, and the graphite amount added was 3% of the total mass. The mixed powder was molded to particles of 20-40 meshes and the obtained particles were heated up to 500° C. for heat treatment under air atmosphere for 10 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 15 ml of catalyst in volume. The raw material 1-butylene was mixed with vapor and air, and the mixture was preheated to 300° C. before passing through the catalyst bed under the following conditions: reaction space velocity of 1-butylene: 400 h$^{-1}$; reaction temperature: 350° C.; the molar ratio between air and butylene: 3.6; and the molar ratio between vapor and butylene: 10; the reaction was steady after 100 hours and the tail gas was analyzed online with gas phase chromatography.

Calculated with the above mentioned formulas, the conversion of 1-butylene was 92.5% and the selectivity to butadiene was 96.5%.

COMPARISON EXAMPLE 1

1. Preparation of Catalyst 404 g of ferric nitrate nonahydrate, 119 g of zinc nitrate hexahydrate, 5.37 g of manganese nitrate solution with a concentration of 50% (by weight) were weighted and dissolved in 1000 ml of distilled water (25° C.), wherein the molar ratio of Fe, Zn and Mn was 1:0.4:0.015; to the solution was added ammonia with a concentration of 20 mol/l dropwise until the pH of the solution reached 7.5. After the addition, the slurry was heated up to 70° C. and stirred for 1 hour before cooling to 25° C., and then filtered, washed to neutral with distilled water.

The obtained filter cake was placed in an oven at 110° C. for drying for 24 hours. The dried solid was subjected to grind, and sieve to give a powder smaller than 80 meshes and then heated up to 650° C. for heat treatment under air atmosphere for 6 hours to give a ferrite precursor powder.

The obtained ferrite precursor powder was homogeneously mixed with graphite by a mechanical agitator, wherein the graphite amount added was 3% of the total mass. The mixed powder was molded to particles of 20-40 meshes and the obtained particles were heated up to 500° C. for heat treatment under air atmosphere for 10 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 15 ml of catalyst in volume. The raw material 1-butylene was mixed with vapor and air and the mixture was preheated to 300° C. before passing through the catalyst bed under the following conditions: reaction space velocity of 1-butylene: 400 h$^{-1}$; reaction temperature: 350° C.; the molar ratio between air and butylene: 3.6; the molar ratio between vapor and butylene: 10; the reaction was steady after 100 hours and the tail gas was analyzed online with gas phase chromatography.

Calculated with the above mentioned formulas, the conversion of 1-butylene was 80.5% and the selectivity to butadiene was 93.2%.

EXAMPLE 2

1. Preparation of Catalyst 404 g of ferric nitrate nonahydrate, 119 g of zinc nitrate hexahydrate, 5.37 g of manganese nitrate solution with a concentration of 50% (by weight) were weighted and dissolved in 1000 ml of distilled water (25° C.), wherein the molar ratio of Fe, Zn and Mn was 1:0.4:0.015; to the solution was added ammonia with a concentration of 20 mol/l dropwise until the pH of the solution reached 7.5. After the addition, the slurry was heated up to 70° C. and stirred for 1 hour before cooling to 25° C., and then filtered, washed to neutral with distilled water.

The obtained filter cake was placed in an oven at 110° C. for drying for 24 hours. The dried solid was subjected to grind, and sieve to give a powder smaller than 80 meshes and then heated up to 650° C. for heat treatment under air atmosphere for 6 hours to give a ferrite precursor powder.

The obtained ferrite precursor powder was homogeneously mixed with aluminium dihydrogen phosphate powder and graphite by a mechanical agitator, wherein the weight ratio between aluminum dihydrogen phosphate powder and ferrite precursor powder was 2:1, and the graphite amount added was 3% of the total mass. The mixed powder was molded to particles of 20-40 meshes and the obtained particles were heated up to 500° C. for heat treatment under air atmosphere for 10 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 15 ml of catalyst in volume. The raw material 1-butylene was mixed with vapor and air and the mixture was preheated to 300° C. before passing through the catalyst bed under the following conditions: reaction space velocity of 1-butylene: 400 h$^{-1}$; reaction temperature: 350° C.; the molar ratio between air and butylene: 3.6; and the molar ratio between vapor and butylene: 10; the reaction was steady after 100 hours and the tail gas was analyzed online with gas phase chromatography.

Calculated with the above mentioned formulas, the conversion of 1-butylene was 90.5% and the selectivity to butadiene was 96.8%.

COMPARISON EXAMPLE 2

1. Preparation of Catalyst 404 g of ferric nitrate nonahydrate, 119 g of zinc nitrate hexahydrate, 5.37 g of manganese nitrate solution with a concentration of 50% (by weight) were weighted and dissolved in 1000 ml of distilled water (25° C.), wherein the molar ratio of Fe, Zn and Mn was 1:0.4:0.015; to the solution was added ammonia with a concentration of 20 mol/l dropwise until the pH of the solution reached 7.5. After the addition, the slurry was heated up to 70° C. and stirred for 1 hour before cooling to 25° C., and then filtered, washed to neutral with distilled water.

The obtained filter cake was placed in an oven at 110° C. for drying for 24 hours. The dried solid was subjected to grind and sieve to give a powder smaller than 80 meshes and then heated up to 650° C. for heat treatment under air atmosphere for 6 hours to give a ferrite precursor powder.

The obtained ferrite precursor powder was homogeneously mixed with aluminum dihydrogen phosphate powder and graphite by a mechanical agitator, wherein the weight ratio between aluminum dihydrogen phosphate powder and ferrite precursor powder was 10:1, and the graphite amount added was 3% of the total mass. The mixed powder was molded to particles of 20-40 meshes and the obtained particles were heated up to 500° C. for heat treatment under air atmosphere for 10 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 15 ml of catalyst in volume. The raw material 1-butylene was mixed with vapor and air and the mixture was preheated to 300° C. before passing through the catalyst bed under the following conditions: reaction space velocity of 1-butylene: 400 h$^{-1}$; reaction temperature: 350° C.; the molar ratio between air and butylene: 3.6; and the molar ratio between vapor and butylene: 10; the reaction was steady after 100 hours and the tail gas was analyzed online with gas phase chromatography.

Calculated with the above mentioned formulas, the conversion of 1-butylene was 493% and the selectivity to butadiene was 97.5%.

COMPARISON EXAMPLE 3

1. Preparation of Catalyst 404 g of ferric nitrate nonahydrate, 119 g of zinc nitrate hexahydrate, 5.37 g of manganese nitrate solution with a concentration of 50% (by weight) were weighted and dissolved in 1000 ml of distilled water (25° C.), wherein the molar ratio of Fe, Zn and Mn was 1:0.4:0.015; to the solution was added ammonia with a concentration of 20 mol/l dropwise until the pH of the solution reached 7.5. After the addition, the slurry was heated up to 70° C. and stirred for 1 hour before cooling to 25° C., and then filtered, washed to neutral with distilled water.

The obtained filter cake was placed in an oven at 110° C. for drying for 24 hours. The dried solid was subjected to grind and sieve to give a powder smaller than 80 meshes and then heated up to 650° C. for heat treatment under air atmosphere for 6 hours to give a ferrite precursor powder.

The obtained ferrite precursor powder was homogeneously mixed with aluminum dihydrogen phosphate powder and graphite by a mechanical agitator, wherein the weight ratio between aluminum dihydrogen phosphate powder and ferrite precursor powder was 0.2:1, and the graphite amount added was 3% of the total mass. The mixed powder was molded to particles of 20-40 meshes and the obtained particles were heated up to 500° C. for heat treatment under air atmosphere for 10 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 15 ml of catalyst in volume. The raw material 1-butylene was mixed with vapor and air and the mixture was preheated to 300° C. before passing through the catalyst bed under the following conditions: reaction space velocity of 1-butylene: 400 $h^{-1}$; reaction temperature: 350° C.; the molar ratio between air and butylene: 3.6; and the molar ratio between vapor and butylene: 10; the reaction was steady after 100 hours and the tail gas was analyzed online with gas phase chromatography.

Calculated with the above mentioned formulas, the conversion of 1-butylene was 84.2% and the selectivity to butadiene was 93.2%.

EXAMPLE 3

1. Preparation of Catalyst 404 g of ferric nitrate nonahydrate, 104 g of zinc nitrate hexahydrate, 12.8 g of magnesium nitrate hexahydrate, 4.4 g of nickel nitrate hexahydrate were weighted and dissolved in 1000 ml of distilled water (20° C.), wherein the molar ratio of Fe, Zn, Mg and Ni was 1:0.35:0.05:0.015; to the solution was added ammonia with a concentration of 20 mol/l dropwise until the pH of the solution reached 8.0. After stirring for 30 minutes, the slurry was stirred for another 1 hour under 70° C. before cooling to 30° C., and then filtered, washed to neutral.

The obtained filter cake was placed in an oven at 110° C. for drying for 24 hours. The dried solid was subjected to grind and sieve prior to the heat treatment under air atmosphere at 700° C. for 2 hours to give a solid material. The material was then subjected to grind and sieve to obtain a ferrite precursor powder smaller than 100 meshes.

Similarly, the ferric phosphate was grinded and sieved to a powder smaller than 100 meshes. The ferric phosphate powder and the ferrite precursor powder were mixed homogeneously by a mechanical agitator wherein the weight ratio between the ferric phosphate powder and the ferrite precursor powder was 1:2. After the homogeneous mixing, graphite (3% of the total weight) was added and again mixed homogeneously before molding into particles of 20-40 meshes, which was then heated up to 520° C. slowly under air atmosphere for heat treatment for 3 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 10 ml of catalyst in volume. The mixed butylene containing 1-butylene, trans-butylene-2, cis-butylene-2 (25% of 1-butylene, 40% of trans-butylene-2 and 35% of cis-butylene-2 in molar content) was mixed with vapor and air, preheated to 350° C. before passing through the catalyst bed under the following conditions: reaction space velocity of the mixed butylene: 300 $h^{-1}$; reaction temperature: 400° C.; the molar ratio between air and butylene: 3.8; and the molar ratio between vapor and butylene: 16; after the reaction was carried out for 20 hours, the components in tail gas of the reaction was analyzed with gas phase chromatography. Calculated with the above mentioned formulas, the conversion of butylene was 96.5% and the selectivity to butadiene was 95.5%. After the reaction continued for 800 hours, the tail gas of the reaction was analyzed. The conversion of butylene was 95.8% and the selectivity of butadiene was 95.2% after calculation, indicating that the catalyst was provided with good stability.

EXAMPLE 4

1. Preparation of Catalyst 404 g of ferric nitrate nonahydrate, 104 g of zinc nitrate hexahydrate, 12.8 g of magnesium nitrate hexahydrate, and 4.4 g of nickel nitrate hexahydrate were weighted and dissolved in 1000 ml of distilled water (20° C.), wherein the molar ratio of Fe, Zn, Mg and Ni was 1:0.35:0.05:0.015; to the solution was added ammonia with a concentration of 20 mol/l dropwise until the pH of the solution reached 8.0. After stirring for 30 minutes, the slurry was stirred for another 1 hour under 70° C. before cooling to 30° C., and then filtered, washed to neutral.

The obtained filter cake was placed in an oven at 110° C. for drying for 24 hours. The dried solid was subjected to grind and sieve prior to the heat treatment under air atmosphere at 700° C. for 2 hours to give a solid material. The material was then subjected to grind and sieve to obtain a ferrite precursor powder smaller than 100 meshes.

Ferric phosphate was grinded and sieved to a powder smaller than 100 meshes; and calcium phosphate was grinded and sieved to a powder smaller than 100 meshes. The three powders were mixed homogeneously by a mechanical agitator wherein the weight ratio of the ferrite precursor powder, ferric phosphate powder and calcium phosphate powder was 1:1:2. After the homogeneous mixing, graphite (3% of the total weight) was added and again mixed homogeneously before molding into particles of 20-40 meshes, which was then first heated up to 500° C. slowly under air atmosphere for heat treatment for 5 hours and then switch to nitrogen and heated up to 600° C. for heat treatment for another 5 hours to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 10 ml of catalyst in volume. The mixed butylene containing 1-butylene, trans-butylene-2, cis-butylene-2 (25% of 1-butylene, 40% of trans-butylene-2 and 35% of cis-butylene-2 in molar content) was mixed with vapor and air, and the mixture was preheated to 350° C. before passing through the catalyst bed under the following conditions: reaction space velocity of the mixed butylene: 300 $h^{-1}$; reaction temperature: 400° C.; the molar ratio between air and butylene: 3.8; and the molar ratio between vapor and butylene: 16; after the reaction was carried out for 20 hours, the components in tail gas of the reaction was analyzed with gas phase chromatography. Calculated with the above mentioned formulas, the conversion of butylene was 96.5% and the selectivity to butadiene was 95.5%. After the reaction continued for 800 hours, the tail gas of the reaction was analyzed. The conversion of butylene was 93.5% and the selectivity of butadiene was 95.8% after calculation.

EXAMPLE 5

1. Preparation of Catalyst 404 g of ferric nitrate nonahydrate, 119 g of zinc nitrate hexahydrate, 5.82 g of cobalt nitrate hexahydrate, 5.37 g of manganese nitrate solution with a concentration of 50% (by weight) were weighted and dissolved in 1000 ml of distilled water (30° C.), wherein the molar ratio of Fe, Zn, Co and Mn was 1:0.4:0.02:0.015, and then to the solution was added trimethylamine solution with a concentration of 1.0 mol/l dropwise until the pH of the solution reached 7.0. After the addition, the slurry was heated up to 70° C. and stirred for 2 hours before cooling to 30° C., and then filtered, washed to neutral.

The obtained filter cake was placed in an oven at 110° C. for drying for 24 hours. The dried solid was heated up to 600° C. under air atmosphere for heat treatment for 10 hours to give a solid material.

The solid material was subjected to grind and sieve to a ferrite precursor powder smaller than 100 meshes; similarly, the carrier zinc phosphate was grinded and sieved to a powder smaller than 100 meshes. The two powders were mixed homogeneously by a mechanical agitator, wherein the weight ratio between zinc phosphate powder and the ferrite precursor powder was 2:1. After the homogeneous mixing, graphite (3% of the total weight) was added and again homogeneously mixed before molding to particles of 20-40 meshes. The obtained particles were heated up to 550° C. under air atmosphere for heat treatment for 1 hour to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 10 ml of catalyst in volume. The 1-butylene was mixed with vapor and air and the mixture was preheated to 350° C. before passing through the catalyst bed under the following conditions: reaction space velocity of 1-butylene: 600 h$^{-1}$; reaction temperature: 380° C.; the molar ratio between air and butylene: 3.3; and the molar ratio between vapor and butylene: 12.

After the reaction was carried out for 100 hours, the tail gas of the reaction was analyzed with gas phase chromatography. The conversion of 1-butylene was 93.6% and the selectivity to butadiene was 96.8% through calculation.

EXAMPLE 6

1. Preparation of Catalyst 404 g of ferric nitrate nonahydrate, 119 g of zinc nitrate hexahydrate, 8.73 g of cobalt nitrate hexahydrate, 5.37 g of manganese nitrate solution with a concentration of 50% (by weight) were weighted and dissolved in 1000 ml of distilled water (30° C.), wherein the molar ratio of Fe, Zn, Co and Mn was 1:0.4:0.03:0.015, and then to the solution was added trimethylamine solution with a concentration of 1.0 mol/l dropwise until the pH of the solution reached 7.0. After the addition, the slurry was heated up to 70° C. and stirred for 2 hours before cooling to 30° C., and then filtered, washed to neutral.

The obtained filter cake was placed in an oven at 110° C. for drying for 24 hours. The dried solid was heated up to 600° C. under air atmosphere for heat treatment for 10 hours to give a solid material.

The solid material was subjected to grind and sieve to a ferrite precursor powder smaller than 100 meshes; similarly, the carrier zinc phosphate was grinded and sieved to a powder smaller than 100 meshes. The two powders were mixed homogeneously by a mechanical agitator, wherein the weight ratio between zinc phosphate powder and the ferrite precursor powder was 2:1. After the homogeneous mixing, graphite (3% of the total weight) was added and again homogeneously mixed before molding to particles of 20-40 meshes. The obtained particles were heated up to 550° C. under air atmosphere for heat treatment for 1 hour to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 10 ml of catalyst in volume. The 1-butylene was mixed with vapor and air and the mixture was preheated to 350° C. before passing through the catalyst bed under the following conditions: reaction space velocity of 1-butylene: 600 h$^{-1}$; reaction temperature: 380° C.; the molar ratio between air and butylene: 3.3; and the molar ratio between vapor and butylene: 12. After the reaction was carried out for 100 hours, the tail gas of the reaction was analyzed with gas phase chromatography. The conversion of 1-butylene was 91.6% and the selectivity to butadiene was 94.8% through calculation.

COMPARISON EXAMPLE 4

1. Preparation of Catalyst

The preparation process of the catalyst was the same as that in Example 5, except of a reduced calcination temperature, which in detail is:

404 g of ferric nitrate nonahydrate, 119 g of zinc nitrate hexahydrate, 5.82 g of cobalt nitrate hexahydrate, 5.37 g of manganese nitrate solution with a concentration of 50% (by weight) were weighted and dissolved in 1000 ml of distilled water (30° C.), wherein the molar ratio of Fe, Zn, Co and Mn was 1:0.4:0.02:0.015, and then to the solution was added trimethylamine solution with a concentration of 1.0 mol/l dropwise until the pH of the solution reached 7.0. After the addition, the slurry was heated up to 70° C. and stirred for 2 hours before cooling to 30° C., and then filtered, washed to neutral.

The obtained filter cake was placed in an oven at 110° C. for drying for 24 hours. The dried solid was heated up to 200° C. under air atmosphere for heat treatment for 10 hours to give a solid material.

The solid material was subjected to grind and sieve to a ferrite precursor powder smaller than 100 meshes; similarly, the carrier zinc phosphate was grinded and sieved to a powder smaller than 100 meshes. The two powders were mixed homogeneously by a mechanical agitator, wherein the weight ratio between zinc phosphate powder and the ferrite precursor powder was 2:1. After the homogeneous mixing, graphite (3% of the total weight) was added and again homogeneously mixed before molding to particles of 20-40 meshes. The obtained particles were heated up to 250° C. under air atmosphere for heat treatment for 1 hour to obtain the catalyst.

2. The Evaluation of the Catalyst Performance by Dehydrogenation of Butylene

The evaluation of the catalytic performance was carried out in a stainless steel tubular reactor (inner diameter, 10 mm; length, 350 mm), with 10 ml of catalyst in volume. The 1-butylene was mixed with vapor and air and the mixture was preheated to 350° C. before passing through the catalyst bed under the following conditions: reaction space velocity of 1-butylene: 600 h$^{-1}$; reaction temperature: 380° C.; the molar ratio between air and butylene: 3.3; and the molar ratio between vapor and butylene: 12. After the reaction was carried out for 100 hours, the tail gas of the reaction was analyzed with gas phase chromatography. The conversion of 1-butylene was 72.6% and the selectivity to butadiene was 91.8% through calculation.

It can be seen from the above results that, when the catalyst of the invention was used, both the conversion of butylene and the selectivity of butadiene in oxydehydrogenation were evidently improved.

What we claimed is:

1. A ferrite catalyst having a general formula of:

$$x(FeA_aD_bO_c)/yZ$$

wherein,

A is Mg atom, Zn atom or a mixture of both atoms at any ratio;

D is a mixture of Mn with Ni and/or Co atoms;

Z is a catalyst carrier, which is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, and magnesium carbonate;

a=0.01-0.6;

b=0.01-0.30;

c is a number balancing each valence;

x, y represent the amounts of principal catalyst and carrier Z respectively, wherein the weight ratio y/x=0.8:1-7:1, wherein D is mixed with precursor compounds so as to be incorporated in the $FeA_aD_bO_c$.

2. The ferrite catalyst of claim 1, wherein D is the mixture of Mn atom with Ni and/or Co in a molar mixing ratio of Mn atom to Ni and/or Co of 10:1-1:10.

3. The ferrite catalyst of claim 2, wherein the molar mixing ratio of Mn to Ni and/or Co is 5:1-1:5.

4. The ferrite catalyst of claim 1, wherein the catalyst carrier Z is one or more selected from the group consisting of calcium phosphate, aluminum dihydrogen phosphate, ferric phosphate, magnesium phosphate, zinc phosphate, and Mg—Al hydrotalcite.

5. The ferrite catalyst of claim 1, wherein the weight ratio y/x=0.8:1-6:1.

6. The ferrite catalyst of claim 1, wherein y/x=1:1-5:1.

7. A method for preparing the catalyst of claim 1, comprising the following steps:

(1) dissolving chemical precursors of desired components into a solution to obtain a mixed slurry;

(2) adding to the mixed slurry a precipitant to adjust the pH of the mixed slurry to 7.0-9.0, to obtain a precipitated slurry;

(3) obtaining a ferrite precursor powder from the precipitated slurry; and (4) mixing the ferrite precursor powder with a carrier powder that is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, and magnesium carbonate, and calcining under a temperature of 500-600° C. to obtain the catalyst of claim 1.

8. The method of claim 7, wherein the method further comprises after step (2) before step (3):

(2.1) heating the precipitated slurry up to 450-700° C. for heat treatment for 2-24 hours.

9. The method of claim 7, wherein the temperature for calcination in step (3) is 540-560° C.

10. A method for preparing the ferrite catalyst of claim 1, comprising the following steps:

(1) dissolving chemical precursors of desired components and a carrier into a solution to obtain a mixed slurry;

(2) adding to the mixed slurry a precipitant to adjust the pH of the mixed slurry to 7.0-9.0, to obtain a precipitated slurry; and (3) calcining the precipitated slurry under a temperature of 500-600° C. to obtain the catalyst, wherein the ferrite catalyst has a general formula of:

$$x(FeA_aD_bO_c)/yZ$$

wherein,

A is Mg atom, Zn atom or a mixture of both atoms at any ratio;

D is one or more atoms selected from the group consisting of Ni, Co, W, Mn, Ca, Mo and V atom;

Z is a catalyst carrier, which is one or more selected from the group consisting of calcium phosphate, calcium dihydrogen phosphate, aluminum phosphate, aluminum dihydrogen phosphate, ferric phosphate, magnesium phosphate, zinc phosphate, Mg—Al hydrotalcite, calcium carbonate, and magnesium carbonate;

a=0.01-0.6;

b=0-0.30;

c is a number balancing each valence;

x, y represent the amounts of principal catalyst and carrier Z respectively, wherein the weight ratio y/x=0.8:1-7:1.

11. The method of claim 10, wherein the method further comprises after step (2) before step (3):

(2.1) heating the precipitated slurry up to 450-700° C. for heat treatment for 2-24 hours.

12. The method of claim 10, wherein the temperature for calcination in step (3) is 540-560° C.

13. The ferrite catalyst of claim 1, wherein the weight ratio y/x=1.2:1-4:1.

14. The ferrite catalyst of claim 1, wherein the weight ratio y/x=1.5:1-3:1.

* * * * *